United States Patent [19]
de Haan

[11] Patent Number: 6,057,492
[45] Date of Patent: May 2, 2000

[54] PLANTS RESISTANT TO TOSPOVIRUSES

[75] Inventor: Petrus Theodorus de Haan, Enkhuizen, Netherlands

[73] Assignee: Novartis AB, Basel, Switzerland

[21] Appl. No.: 08/913,374

[22] PCT Filed: Mar. 22, 1996

[86] PCT No.: PCT/EP96/01271

§ 371 Date: Sep. 18, 1997

§ 102(e) Date: Sep. 18, 1997

[87] PCT Pub. No.: WO96/29420

PCT Pub. Date: Sep. 26, 1996

[30] Foreign Application Priority Data

Mar. 23, 1995 [GB] United Kingdom .................. 9505907

[51] Int. Cl.[7] .............................. C12N 5/04; C12N 15/33; A01H 1/00; A01H 5/10
[52] U.S. Cl. ...................... 800/280; 435/69.1; 435/320.1; 435/419; 435/468; 536/23.72; 800/279; 800/301; 800/265
[58] Field of Search ...................... 536/23.72; 435/172.3, 435/320.1, 69.1, 410, 419, 468; 800/205, 278, 279, 295, 298, 301, 260, 265, 280

[56] References Cited

U.S. PATENT DOCUMENTS 5,583,021  12/1996  Dougherty et al. ...................... 435/468

FOREIGN PATENT DOCUMENTS

| 0223452 | 5/1987 | European Pat. Off. . |
| 0240332 | 10/1987 | European Pat. Off. . |
| 0426195 | 5/1991 | European Pat. Off. . |
| 0566525 | 10/1993 | European Pat. Off. . |

OTHER PUBLICATIONS

De Haan et al., J. gen. Virol. (1989), 70, pp. 3469–3473.
De Haan et al., Journal of General Virology, (1990), 71, pp. 1001–1007.
German et al., Phytopathology, (1988), 78:1599.
Huguenot et al., Arch Virol, (1990), 110: 47–62.
Kormelink et al., Virology, vol. 200, 1994, pp. 56–65.
Pang et al., Bio/Technology, vol. 11, 1993, pp. 819–824.
Ronco et al., Phytopathology, (1989), 79 (11) pp. 1309–1313.
Wilson, Proc. Natl. Acad. Sci. USA, vol. 90, (1993) pp. 3134–3141.
MacKenzie et al. Resistance to tomato spotted wilt virus infection in transgenic tobacco expressing the viral nucleocapsid gene. Molecular Plant Microbe Interactions. 5(1):34–40, Jan.–Feb. 1992.
Pang et al. Resistance to heterologous isolates of tomato spotted wilt virus in transgenic tobacco expressing its nucleocapsid protein gene. Molecular Plant Pathology. 82(10):1223–1229, Oct. 1992.
Vaira et al. Resistance to tosposviruses in *Nicotiana benthamiana* transformed with the N gene of tomato spotted wilt virus: correlation between transgene expression and protection in primary transformants. Molecular Plant–Microbe Interactions. 8(1):66, Jan.–Feb. 1995.
Prins et al. Broad resistance to tospoviruses in transgenic tobacco plants expressing threee tospoviral nucleoprotein gene sequences. Molecular Plant Microbe Interactions. 8(1):85–91, Jan.–Feb. 1995.
Kormelink et al. The nucleotide sequence of the M RNA segment of tomato spotted wilt virus, a bunyavirus with two ambisense RNA segments. Journal of General Virology. 73:2795–2804, Oct. 1992.
Kormelink et al. The nucleotide sequence of the M RNA segment of tomato spotted wilt virus, a bunyavirus with two ambisense RNA segments. The Journal of General Virology. 74 (Pt. 4):790, Apr. 1993.

*Primary Examiner*—Elizabeth F. McElwain
*Assistant Examiner*—Ashwin Mehta
*Attorney, Agent, or Firm*—Mary K. Hehman; Thomas Hoxie

[57] ABSTRACT

Plant transformation vectors comprising a polynucleotide effective to render resisitance or tolerance to infection by a tospovirus, and a microbiological process for making virus tolerant or resistant plants are provided herein.

20 Claims, 2 Drawing Sheets

PLANTS RESISTANT TO TOSPOVIRUSES

BACKGROUND OF THE INVENTION

The tospoviruses are a group of negative-strand RNA viruses, which form a separate genus within the arthropod-borne family of Bunyaviridae and are unique within this family with respect to their ability to infect plants. Based on serological differences and sequence divergence of the nucleoprotein gene, four different tospovirus species have so far been established: tomato spotted wilt virus (TSWV), tomato chlorotic spot virus (TCSV), groundnut ringspot virus (GRSV), and impatiens necrotic spot virus (INSV). Based on serological data, groundnut bud necrosis virus, watermelon silver mottle virus and groundnut yellow spot virus have been proposed as additional members of the Tospovirus genus.

Tospoviruses are the only plant viruses that are transmitted by thrips species in a propagative manner. The type species of the genus Tospovirus, TSWV, has a very broad host range, encompassing more than 650 plant species within 70 families, including many important crops and ornamentals. The TSWV particle consists of a nucleocapsid core, in which the genomic RNAs are tightly associated with the nucleoprotein (N), surrounded by a lipid membrane containing two types of glycoprotein-protrusions G1 and G2. In addition, several copies of the putative viral RNA-dependent RNA polymerase are present in the virus particle.

The complete nucleotide sequence of the three genomic RNAs of TSWV has been determined. The L RNA is of complete negative polarity and encodes the putative viral polymerase of 331.5 kilodalton (ID). The M and S RNAs both have an ambisense coding arrangement and are translated from subgenomic messenger RNAs. The M RNA codes for the precursor of the membrane glycoproteins G1 and G2 (of 78 kD and 58 kD respectively) and a non-structural protein ($NS_M$) of 33.6 kD, which represents the putative viral movement protein. The S RNA codes for the N protein of 28.8 kD and another non-structural protein ($NS_S$) of 52.4 kD.

When compared to coding arrangements of the genomic RNAs of other members of the family Bunyaviridae, tospoviruses are unique in having an ambisense M RNA segment. The additional presence of the $NS_M$ gene on the viral strand seems to be an evolutionary adaptation of Bunyaviridae to the plant kingdom. It has been proposed that the $NS_M$ gene product enables the virus to pass the cell wall boundary, suggesting $NS_M$ to represent the viral cell-to-cell movement protein.

Engineered resistance to tomato spotted wilt tospovirus (TSWV) has been accomplished previously by expressing the viral nucleoprotein (N) gene in transgenic tobacco. Recently, engineered TSWV resistance has been introduced in tomato plants and tomato hybrids. Similar levels of protection, i.e. complete immunity to the virus in homozygous S2 plants, have been observed when an untranslatable N gene was expressed, indicating that the N gene-based resistance is, at least for a major part, RNA-mediated.

Besides tospoviral nucleoprotein and positive strand RNA virus coat protein sequences, other, non-structural gene sequences have been used to confer engineered virus resistance, including replicase and protease genes.

SUMMARY OF THE INVENTION

The present invention provides, inter alia, recombinant nucleotide sequences based on those encoding the Tospovirus M RNA which are useful in rendering plants tolerant or resistant to tospoviral infections. By "resistant" is meant a plant which exhibits substantially no phenotypic changes as a consequence of infection with the virus. By "tolerant" is meant a plant which, although it may exhibit some phenotypic changes as a consequence of infection with a virus, does not have a substantially decreased reproductive capacity or substantially altered metabolism.

According to the present invention there is provided a recombinant polynucleotide, comprising a transcriptional regulatory region and a region contiguous therewith and under the transcriptional control thereof, wherein the contiguous region comprises the sequence depicted in SEQ ID No. 1 or a sequence complementary thereto or a part of the sequence or complement, characterized in that the sequence, complement or part is modified (i) by removal therefrom of translational-start encoding codons, or mutation of such codons so that they do not encode translational start or stop codons; or (ii) by insertion or deletion of nucleotides 3' of the translational start encoding codon so that the translational reading frame of the thus encoded RNA is different to that of the unmodified sequence, complement or part.

By "part" is meant a sequence contained within the contiguous sequence of the recombinant polynucleotide according to the invention, and having at least 80 nucleotides. More preferably the part has at least 150 nucleotides, and still more preferably the part has at least 400 nucleotides.

In the case that the translational start encoding codon is rendered non functional, it is preferred that the said mutation consists of base replacement. It is preferred that the contiguous region consists of nucleotides 3813 to 4721 in SEQ ID. No. 1 or the complement thereof or a part of the sequence or complement.

The invention also includes recombinant polynucleotides wherein in the contiguous region, the sequence depicted in SEQ ID No. 1 from nucleotides 3813 to 4721 has been modified so as to comprise codons other than those present in the unmodified sequence, with the proviso that in the modified sequence, the amino acids specified by such codons are the same as those specified by the codons in the unmodified sequence.

The invention further includes a nucleotide sequence which is complementary to one (hereinafter "test" sequence) which hybridizes under stringent conditions with the contiguous region of the said polynucleotides, as well as RNA which is encoded by the said contiguous region or nucleotide sequence. When the hybridization is performed under stringent conditions, either the test or inventive sequence is preferably supported. Thus either a denatured test or inventive sequence is preferably first bound to a support and hybridization is effected for a specified period of time at a temperature of between 55 and 70° C. in double strength citrate buffered saline containing 0.1% SDS followed by rinsing of the support at the same temperature but with a buffer having a reduced SC concentration. Depending upon the degree of stringency required such reduced concentration buffers are typically single strength SC containing 0.1% SDS, half strength SC containing 0.1% SDS and one tenth strength SC containing 0.1% SDS.

The invention still further includes: a DNA construct comprising the said polynucleotide or nucleotide sequence; a biological vector comprising the said polynucleotide, nucleotide sequence, or construct; and plant cells containing the polynucleotide, nucleotide sequence, construct, or vector.

The invention still further includes a method of rendering plants resistant or tolerant to infection by tospoviruses comprising the steps of transforming regenerable plant material with a recombinant polynucleotide comprising a transcriptional regulatory region and a region contiguous therewith and under the transcriptional control thereof and regenerating the thus transformed material into morphologically normal plants, characterized in that the recombinant polynucleotide comprises as its contiguous sequence, the sequence depicted in SEQ ID No. 1 or a sequence complementary thereto or a part of the sequence or its complement. It is more preferred that the contiguous sequence comprises the sequence depicted in SEQ ID No. 1 or a sequence complementary thereto or a part of the sequence or complement, which is modified (i) by removal therefrom of translational-start encoding codons, or mutation of such codons so that they do not encode translational start or stop codons; or (ii) by insertion or deletion of nucleotides 3' of the translational start encoding codon so that the translational reading frame of the thus encoded RNA is different to that of the unmodified sequence, complement or part (as indicated above). Such a modified sequence may further contain the other modifications indicated above with respect to length and altered codon usage.

The said normal fertile plants which result from the method indicated in the immediately preceding paragraph may be selfed to yield products from which are selected those which exhibit resistance or tolerance to tospoviral infection thereby yielding a substantially homogeneous line with respect to this trait. Individuals of the said line, or the progeny thereof, may be crossed with plants which optionally exhibit the said trait. In a particular embodiment of the method, the selfing and selection steps are repeated at least five times in order to obtain the homogeneous line.

The contiguous region may be bounded by a plant effective transcriptional promoter and terminator, wherein the promoter and terminator control transcription of the sequence or complement when it is incorporated into a plant genome. Whatever recombinant sequence according to the invention it is intended to introduce into plants, such introduction may be via a bacterial or viral vector, by microinjection, by co-incubation of the plant material and polynucleotide, sequence or construct in the presence of a high molecular weight glycol, or by coating of the polynucleotide, sequence or construct onto the surface of biologically inert particle which is then introduced into the material.

The invention still further includes the use of a recombinant polynucleotide comprising the sequence depicted in SEQ ID No. 1 or a sequence complementary thereto or a part of said sequence or complement in the manufacture of virus resistant or tolerant plants. It is more preferred that the contiguous sequence comprises the sequence depicted in SEQ ID No. 1 or a sequence complementary thereto or a part of the sequence or complement, which is modified (i) by removal therefrom of translational-start encoding codons, or mutation of such codons so that they do not encode translational start or stop codons; or (ii) by insertion or deletion of nucleotides 3' of the translational start encoding codon so that the translational reading frame of the thus encoded RNA is different to that of the unmodified sequence, complement or part (as indicated above). Such a modified sequence may further contain the other modifications indicated above with respect to length and altered codon usage.

The invention still further includes a virus tolerant or resistant plant having stably integrated and expressed within its genome, a recombinant polynucleotide comprising the sequence depicted in SEQ ID No. 1 or a sequence complementary thereto or a part of said sequence or complement. It is more preferred that the contiguous sequence comprises the sequence depicted in SEQ ID No. 1 or a sequence complementary thereto or a part of the sequence or complement, which is modified (i) by removal therefrom of translational-start encoding codons, or mutation of such codons so that they do not encode translational start or stop codons; or (ii) by insertion or deletion of nucleotides 3' of the translational start encoding codon so that the translational reading frame of the thus encoded RNA is different to that of the unmodified sequence, complement or part (as indicated above). Such a modified sequence may further contain the other modifications indicated above with respect to length and altered codon usage.

Virus resistant or tolerant plants according to the invention include field crops, vegetables and fruits including tomato, pepper, melon, lettuce, cauliflower, broccoli, cabbage, brussels sprout, sugar beet, corn, sweetcorn, onion, carrot, leek, cucumber, tobacco, alfalfa, aubergine, beet, broad bean, celery, chicory, cow pea, endive, gourd, groundnut, papaya, pea, peanut, pineapple, potato, safflower, snap bean, soybean, spinach, squashes, sunflower, sorghum, water-melon and the like; and ornamental crops including Impatiens, Begonia, Petunia, Pelargonium, Viola, Cyclamen, Verbena, Vinca, Tagetes, Primula, Saint Paulia, Ageratum, Amaranthus, Anthirrhinum, Aquilegia, Chrysanthemum, Cineraria, Clover, Cosmo, Cowpea, Dahlia, Datura, Delphinium, Gerbera, Gladiolus, Gloxinia, Hippeastrum, Mesembryanthemum, Salpiglossis, Zinnia, and the like.

The invention still further includes the progeny of above mentioned plants, which contain the contiguous sequence stably incorporated and hereditable in a Mendelian manner, and/or the seeds of such plants or such progeny. The skilled man will recognize that the invention thus includes the use of the above mentioned plants or seeds or progeny in the manufacture of all plants, including varieties.

The invention still further includes a microbiological process of making virus tolerant or resistant plants, including varieties thereof, comprising the steps of: (i) transforming regenerable plant material with a recombinant polynucleotide and regenerating the thus transformed material into morphologically normal fertile plants; and (ii) optionally crossing the plants resulting from (i) with plants which are not the product of (i); characterized in that the recombinant polynucleotide comprises the sequence depicted in SEQ ID No. 1 or a sequence complementary thereto or a part of the sequence or its complement. It is more preferred that the contiguous sequence comprises the sequence depicted in SEQ ID No. 1 or a sequence complementary thereto or a part of the sequence or complement, which is modified (i) by removal therefrom of translational-start encoding codons, or mutation of such codons so that they do not encode translational start or stop codons; or (ii) by insertion or deletion of nucleotides 3' of the translational start encoding codon so that the translational reading frame of the thus encoded RNA is different to that of the unmodified sequence, complement or part (as indicated above). Such a modified sequence may further contain the other modifications indicated above with respect to length and altered codon usage. In a particular embodiment of the process, the said normal fertile plants are selfed to yield products from which are selected those that exhibit resistance or tolerance to tospoviral infection thereby yielding a substantially homogeneous line with respect to this trait. Individuals of the said line, or the progeny thereof, may be crossed with plants optionally exhibiting the said trait. It is preferred that the selfing and selection steps are repeated at least five times in order to obtain the homogeneous line.

By "microbiological process" is meant any process involving or performed upon or resulting in microbiological material and thus includes a process consisting of a succession of steps at least one of which steps is micro-biological. Transformation of plant material with inter alia, viral, and bacterial vectors (*Agrobacterium tumefaciens* for example), nucleic acid coated particles, and nucleic acid per se (optionally suspended in a high molecular weight glycol) are all microbiological processes.

The invention will be further apparent from the following description taken in conjunction with the associated Sequence Listing and Figures. The Example demonstrates that high levels of resistance of plants to the negative-strand tomato spotted wilt virus are obtained in transgenic tobacco expressing sequences derived from the putative viral movement protein gene, $NS_M$, which is encoded by nucleotides 3813 to 4721 in the sequence depicted in SEQ ID No. 1.

In the Sequence Listing:

SEQ ID. No. 1 shows the DNA sequence complementary to one which encodes the tospoviral M-RNA sequence which itself encodes the putative viral movement protein, in this case from tomato spotted wilt virus;

SEQ ID. No. 2 shows sequence of the primer designated as Zup051 encoding the sequence from nucleotides 108 to 129 of the viral M RNA;

SEQ ID. No. 3 shows the sequence of the primer designated as Zup014 encoding the sequence from nucleotides 3779 to 3800 of the viral complementary M RNA;

SEQ ID. Nos. 4 and 5 show the duplex of the EcoRI/BamHI linker ligated to the sequence shown in SEQ ID No. 2.

BRIEF DESCRIPTION OF THE FIGURES

FIGS. 1 (A–C) shows the construction of plant transformation vectors pTSWV $NS_M$-A, pTSWV $NS_M$-B and pTSWV $NS_M$-C. $NS_M$ sequences are amplified from a genomic cDNA clone of TSWV, using primers that added a BamHI restriction site to the 3' end of the gene (Zup014) and a EcoRI site immediately downstream of the original startcodon (Zup051). An oligonucleotide linker sequence containing an in frame startcodon is ligated to the 5' end of the PCR fragment, thereby restoring the $NS_M$ ORF. Directly upstream of the ATG a unique KpnI site is present. This fragment is inserted in the BamHI site of a pUC18 vector, resulting in a PstI site 3' of the $NS_M$ sequence. By treating KpnI linearised DNA with T4 DNA polymerase, blunt ends are created to which PstI linkers are ligated prior to cloning the $NS_M$ gene as a PstI fragment in the PstI site of the pZU-A plasmid in both sense (A) and anti-sense orientation (C), in the pTSWV $NS_M$-A construct, the pZU-A vector had been previously supplied with TMV translation enhancing sequences upstream of the cloning site. Incubation with T4 DNA polymerase for a longer time at an elevated temperature results in the removal of extra nucleotides by the exonuclease activity of T4 DNA polymerase: these extra nucleotides included the A residue of the $NS_M$ startcodon. Ligation of a PstI linker yields an ATG-deficient $NS_M$ sequence, which is hence not translatable (B). After cloning in the PstI site of the pZU-A vector, the $NS_M$ sequences are supplied with a CaMV 35S promoter at the 5' end and flanked at their 3' ends by a nopaline synthase terminator. Finally, all three $NS_M$ constructs are cloned in the KpnI and SmaI sites of binary vector pBIN19. B=BamHI; E=EcoRI; K=KpnI; P=PstI; 4=blunt after treatment with T4 DNA polymerase. RB and LB are right and left border sequences respectively. The ΔATG indicates removal of the ATG startcodon.

DETAILED DESCRIPTION OF THE INVENTION

MATERIALS AND METHODS

All manipulations involving DNA or RNA are performed according to standard procedures (Sambrook et al. 1989).
Viruses and Plants The different tospovirus strains, i.e. TSWV strain BR-01, TCSV strain BR-03, and GRSV strain SA-05, have been described by Avila et al. (1990, 1992 and 1993) and are maintained on systemic hosts *Nicotiana rustica* var. America or *N. tabacum* var. SR1. Recipient plants used in the transformation experiments are *N. tabacum* var. SR1 plants. All manipulations with transgenic plant material are carried out under conditions (PKII) imposed by the Dutch authorities (VROM/COGEM).

Construction of $NS_M$ Gene Sequence Expression Vectors $NS_M$ gene sequences of TSWV (Kormelink et al. 1992a), are modified in such a way that an EcoRI site is generated immediately downstream of the original startcodon, using primer Zup051 (dGG GAATTCTTTTCGGTAACAAGAGGCC) SEQ ID NO:2 located at position 108 to 129 of the viral M RNA and Zup014 (dCCCTGCA GGATCCGAAATTTAAGCTTAAATAAGTG), SEQ ID NO:3 located at position 1043 to 1023 of the viral complementary M RNA. The resulting PCR fragment is digested with EcoRI and a EcoRI/BamHI linker including an internal KpnI site and an in frame start codon

```
         5' GATCCGGCAACGAAGGTACCATGGG 3'
    3'     GCCGTTGCTTCCATGGTACCCTTAA 5'
      BamHI          KpnI NcoI EcoRI
``` is ligated. This slightly modified $NS_M$ gene (starting with amino acid sequence Met-Leu-Ile . . . instead of Met-Thr-Val . . .) is cloned in a pUC18 vector as a BamHi restriction fragment. The resulting plasmid is linearised using KpnI, and PstI linkers are ligated after creating blunt ends using T4 DNA polymerase. The 5' to 3' exonuclease activity of T4 DNA polymerase is used to create an untranslatable $NS_M$ sequence devoid of its start codon. Different reaction temperatures and incubation times are used to vary the extent of 5' to 3' exonuclease degradation. The resulting clones are checked by sequence analyses and a clone is selected in which the original start codon is mutagenised to CTG. The PstI restriction fragments, i.e. one with an in-frame ATG startcodon and the mutant, are ligated in plant transformation vector pZU-A (Gielen et al. 1991) between the CaMV 35S promoter and the nopaline synthase (nos) terminator. In the pTSWV $NS_M$-A construct, the untranslated leader sequence of TMV (Gallie et al. 1987) is inserted immediately upstream of the $NS_M$ gene. In addition, an anti-sense construct is selected. Finally, three $NS_M$ constructs are inserted in binary vector pBIN19 (Bevan 1984), yielding pTSWV $NS_M$-A (sense polarity), pTSWV $NS_M$-B (sense/untranslatable) and pTSWV $NS_M$-C (anti-sense polarity). Details of this cloning schedule are presented in FIG. 1.

Transformation of Tobacco

Figure 1:
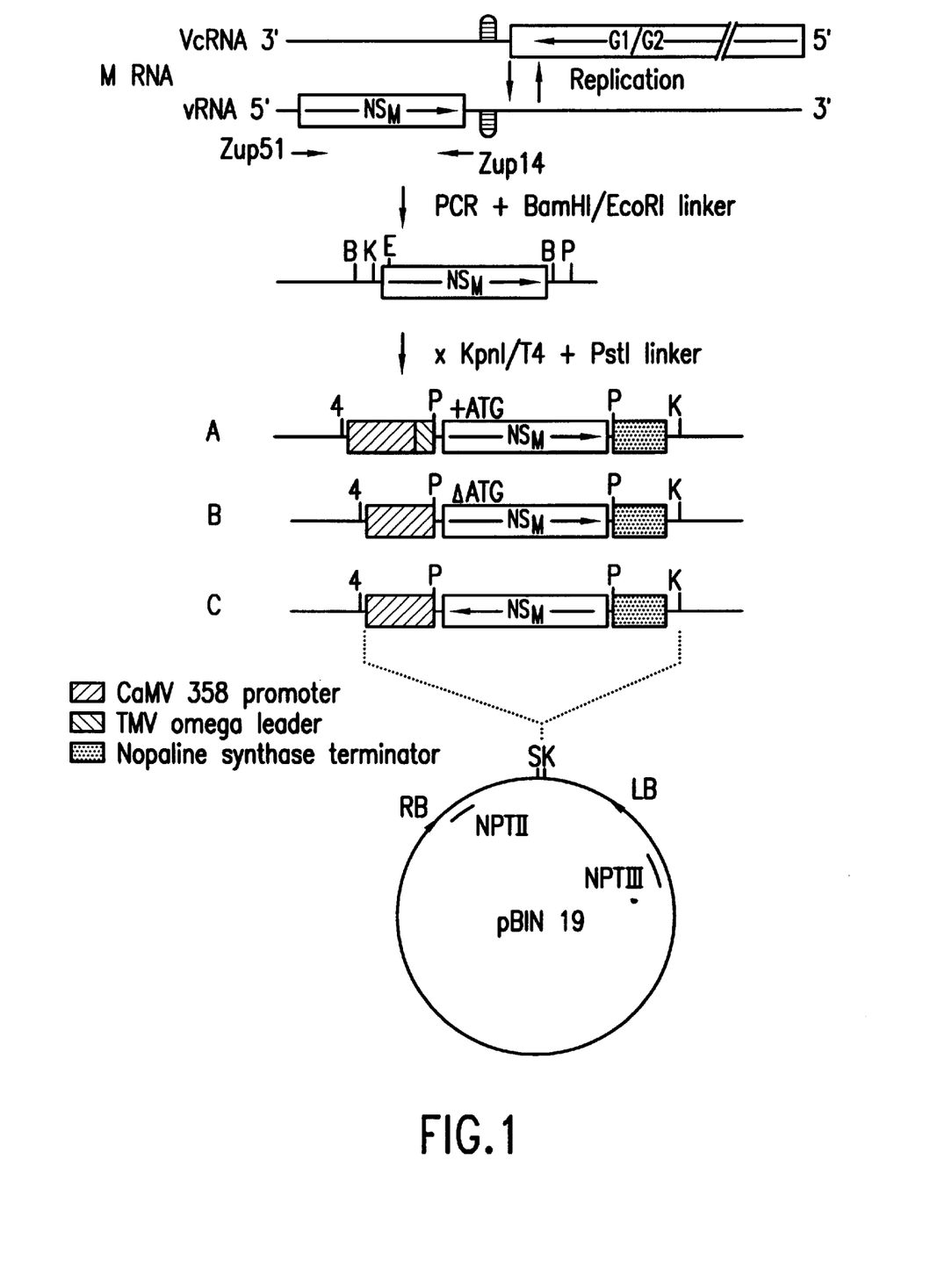
Figure 2:
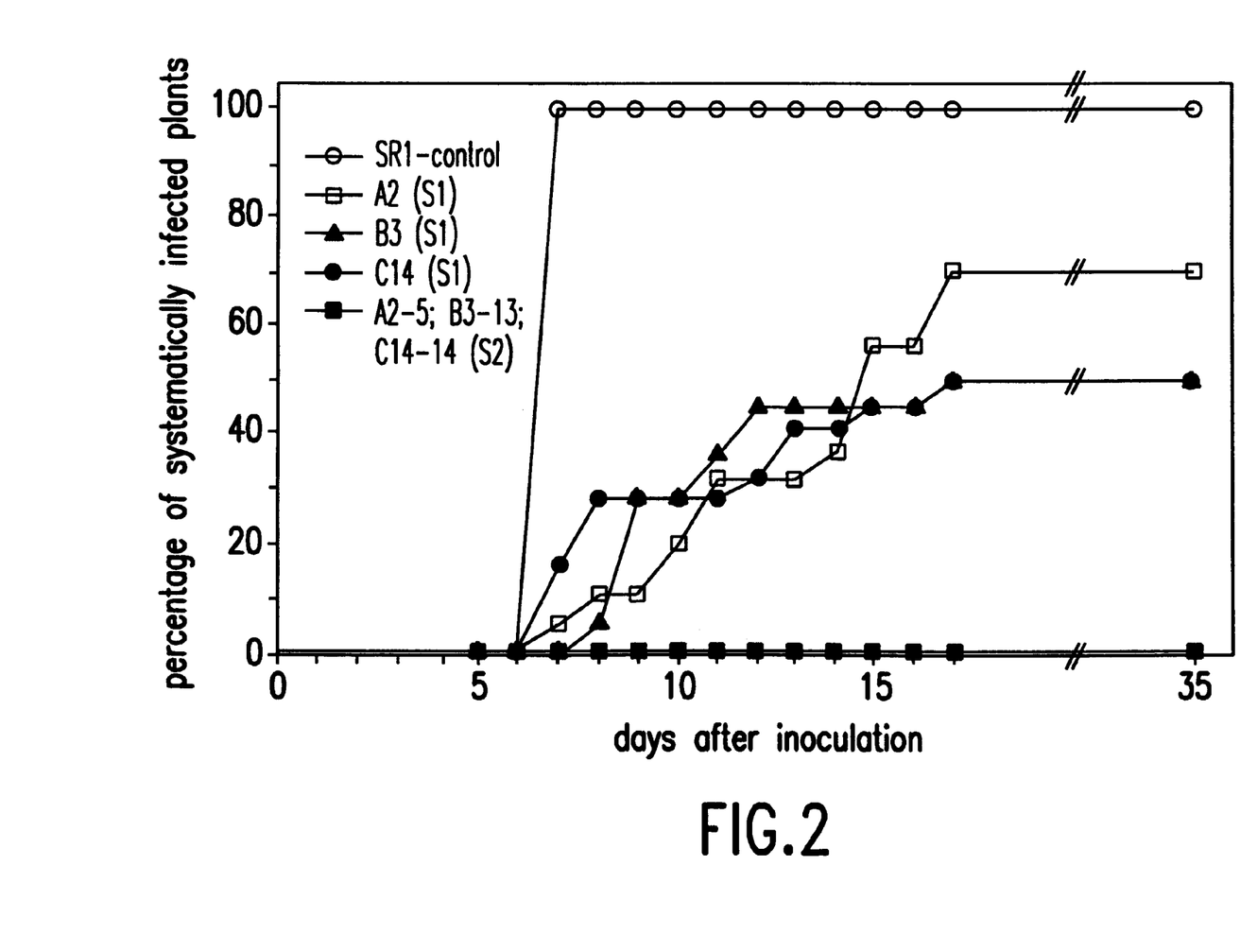
FIG. 2 shows the development of systemic symptoms in transgenic tobacco plants expressing TSWV movement protein ($NS_M$) sequences. The best performing S1 lines of the three different groups of transformants are indicated (A2, B3 and C14), as well as some S2 lines derived plants from these S1 lines that show complete immunity to tomato spotted wilt virus (lines A2-5, B3-13 and C14-14). Plants from a segregant line that lacks transgenic sequences are used as a TSWV-susceptible control.

FIG. 1 shows three constructs containing cDNA sequences derived from the TSWV $NS_M$ gene. Construct pTSWV $NS_M$-A contains the $NS_M$ gene in a translatable form cloned behind a CaMV 35S promoter supplied with translational enhancing sequences of TMV. Construct pTSWV $NS_M$-B contains the $NS_M$ gene of which the original ATG start codon is replaced by CTG. Hereby, a non-translatable form of this gene is created, since the first downstream ATG codon in the $NS_M$ sequence is located out of frame, 52 nucleotides downstream of the original ATG which results in the translation of a peptide of only 4 amino acid residues in length. In the pTSWV $NS_M$-C construct $NS_M$ sequences are cloned in such a way that an anti-sense RNA with respect to the viral M RNA segment and the $NS_M$ mRNA is produced in planta. At the 3' end of all $NS_M$ sequences the transcription-termination signal of the nopaline synthase (nos) gene is ligated. Subsequently, the three $NS_M$ gene sequence expressor cassettes are each cloned into the binary vector pBIN19. The pBIN19-derived vectors pTSWV $NS_M$-A, pTSWV $NS_M$-B and pTSWV $NS_M$-C are introduced into *Agrobacterium tumefaciens* strain LB4404 (Ditta et al. 1980) by triparental mating, using pRK2013 (Horsch et al. 1985) as a helper plasmid. *N. tabacum* var. SR1 plants are transformed via *A. tumefaciens*-mediated leaf disk transformation, and the transformants are regenerated as described by Horsch et al. (1985).

Analysis of Protection of Transgenic Plants Against TSWV

S1 progeny seeds are collected from 30 original pTSWV $NS_M$-A transformed plants, 26 pTSWV $NS_M$-B transformed plants and 24 pTSWV $NS_M$-C plants. Resulting 80 S1 lines are assayed for resistance to TSWV and all resistant plants are maintained for seed production. Twenty plants from the S2 progeny lines are subsequently inoculated with TSWV. Finally, plants from TSWV resistant S2 lines are also challenged with tospoviruses TCSV and GRSV. Inoculations are performed according to standard procedures (Gielen et al. 1991).

The appearance of systemic symptoms is monitored on a daily basis until day 35 after inoculation. Plants are scored susceptible when leaves younger than the inoculated leaf showed characteristic tospovirus induced symptoms i.e. severe stunting and chlorosis, usually followed by death of the plant within a week. Leaf samples from visually healthy plants are collected to check for the presence of the $NS_S$ gene product by ELISA, using a polyclonal antisera directed against TSWV $NS_S$ protein (Kormelink et al. 1991). This antiserum recognizes the $NS_S$ proteins of established tospoviruses TSWV, TCSV and GRSV.

Resistance Levels in Transgenic Tobacco Plants

In total, 93 transformed plants are obtained that express $NS_M$-derived sequences. Of these plants, 34 contain pTSWV $NS_M$-A sequences, 26 the pTSWV $NS_M$-B insert and 24 transformants are obtained expressing pTSWV $NS_M$-C. All original transformants are maintained for seed production. Twenty plants of the resulting S1 progenies are subsequently assayed for resistance to TSWV. Resistant plants are maintained for S2 seed production and resulting S2 plants are tested for their ability to resist infection by TSWV. Four of the pTSWV $NS_M$-A transformed plants show virus disease-like symptoms during their development. From the four original transformants one plant is unable to set seed, therefore no progeny can be tested. Thirty S1 lines, derived from the remaining transformants are tested and four display resistance to TSWV (Table 1). From the progenies of those plants, six lines display complete immunity to TSWV.

TABLE 1

Resistance levels in $NS_M$ sequence expressing transgenic tobacco S1 plants and S2 progenies

| | S1 line | #resistant/#tested | immune S2 progenies |
|---|---|---|---|
| pTSWV $NS_M$-A | A2 | 6/20 | 4/6 |
| | A13 | 2/20 | 0/2 |
| | A23 | 5/20 | 0/5 |
| | A30 | 2/20 | 2/2 |
| | 26 others | 0/20 | — |
| pTSWV $NS_M$-B | B3 | 10/20 | 4/10 |
| | 25 others | 0/20 | — |
| pTSWV $NS_M$-C | C14 | 10/20 | 3/10 |
| | C22 | 3/20 | 3/3 |
| | 22 others | 0/20 | — |

Of the 26 S1 lines transformed with the pTSWV $NS_M$-B construct, only one shows resistance to the virus, albeit at a considerable level of 50% in the S1 generation. In four of the resulting ten S2 lines complete immunity is observed. In two of the segregating pTSWV $NS_M$-C lines resistance levels of up to 50% are observed. Resistance levels of up to 100% (i.e. immunity) are reached in six of the resulting S2 lines.

Expression of $NS_M$ Specific RNA and Protein in Transgenic Plants

The transcriptional expression of $NS_M$ sequences in all seven S1 lines that displayed resistance to the virus (A5, A13, A23, A30, B3, C14 and C22) was checked by Northern blot analysis, using a $^{32}$P-DATP labeled double stranded $NS_M$ cDNA probe. In all resistant lines, transgenically produced RNA could be detected (results not shown), at a level comparable to that reported previously for resistant N gene sequence expressors (De Haan et al. 1992). In leaf-extracts from pTSWV $NS_M$-A transformed plants, $NS_M$ protein could neither be observed by Western blot analyses, nor when ELISA techniques were used. $NS_M$ protein, however, was observed in cell wall-enriched fractions derived from some of these plants, indicating that the protein accumulates to low levels in cell wall material.

The results given inter alia, in Table 1 above indicate that besides expression of N gene sequences of TSWV, also expression of sequences derived from its $NS_M$ gene, the putative tospoviral movement protein gene, are able to confer resistance in transgenic tobacco plants to similar high levels as plants expressing nucleoprotein gene sequences (Gielen et al. 1991; De Haan et al. 1992; Prins et al. 1994).

Because of the removal of the original startcodon, and the presence of an out of frame ATG start codon, $NS_M$ protein cannot be detected in any of the pTSWV $NS_M$-B lines. The same holds true for the anti-sense expressing pTSWV $NS_M$-C lines. In addition, the majority of pTSWV $NS_M$-A transformed plants do not accumulate detectible amounts of $NS_M$ protein. Plants that do express $NS_M$ protein to a detectable level always develop morphological aberrations, indicating that high levels of expression of the protein may have a negative effect on the growth of the plant. Only plants that do not express the protein or express protein at undetectably low levels develop normally.

The high levels of resistance in plants expressing untranslatable and anti-sense RNA support the view that the transgenically expressed RNA, rather than the protein, confers the observed resistance. Resistance induced by $NS_M$ sequences results in immunity to TSWV in the homozygous S2 progeny lines.

A number of theories have been proposed for the mechanism of such RNA-mediated resistance. The transgenically produced RNA may interact with the incoming viral RNA or replicative forms of the virus by an anti-sense mechanism. Another model implies competition between transgenic RNAs and viral RNAs for essential plant or viral factors involved in virus replication.

Although the invention has been particularly described with reference to the production of transgenic tobacco resistant to tospoviral infection, it will be appreciated that the invention is not limited to this Example. In particular, any plant species susceptible to tospoviral infection may be rendered resistant or tolerant according to the present disclosure. Moreover, the method of the invention is, of course, not limited to the use of the precise transformation techniques and constructs disclosed in the Examples.

REFERENCES

Avila, A. de, Huguenot, C., Resende, R. de O., Kitajima, E. W., Goldbach, R. W., & Peters, D. (1990) *J. Gen. Virol.* 71 pp2801–2807.

Avila, A. C. de, De Haan, P., Smeets, M. L. L., Resende, R. de O., Kormelink, R., Kitajima, E. W., Goldbach, R. W., and Peters, D. (1992) *Arch. Virol.* 128 pp211–227.

Avila, A. C. de, De Haan, P., Kormelink, R., Resende, R. de O., Goldbach, R. W., and Peters, D. (1993) *J. Gen. Virol.* 74 pp153–159.

Bevan, M. (1984) *Nucl. Acids Res.* 12 pp8711–8722.

Ditta, G., Stanfield, S., Corbin, D., and Helsinki, D. R. (1980) *Proc. Natl. Acad. Sci.* USA 77 pp7347–7351.

Gallie, D. R., Sleat, D. E., Watts, J. W., Turner, P. C. (1987) *Nucl. Acids Res.* 15 pp8693–8711.

Gielen, J. J. L., De Haan, P., Kool, A. J., Peters, D., Van Grinsven, M. Q. J. M., and Goldbach, R. W. (1991) *Bio/Technology* 9 pp1363–1367.

Horsch, R. B., Fry, J. E., Hoffmann, N. L., Eichholtz, D., Rogers, S. G. and Fraley, R. T. (1985) *Science* 227 pp1229–1231.

Kormelink, R., Kitajima, E. W., De Haan P., Zuidema, D., Peters, D., and Goldbach R. (1991) *Virology* 181 pp459–468.

Kormelink, R., De Haan, P., Meurs, C., Peters, D. and Goldbach, R. (1992) *J. Gen. Virol.* 73 pp2795–2804.

Kormelink, R., De Haan, P., Peters, D., and Goldbach, R. (1992) J. Gen. Virol. 73 pp687–693

Sambrook, J., Fritsch, E. F., and Maniatis, T. (1989) in "Molecular cloning: A laboratory manual", 2nd ed. (Cold Spring Harbor, New York: Cold Spring Harbor Laboratory).

---

We claim:

1. A plant transformation vector comprising a polynucleotide effective to render a plant resistant or tolerant to infection by a tospovirus wherein the polynucleotide hybridizes under stringent conditions to a polynucleotide having the sequence of SEQ ID NO.: 1, and wherein the polynucleotide is operatively linked to a plant effective transcriptional promoter.

2. Transgenic plant cells comprising the vector of claim 1.

3. A transgenic plant comprising a transgenic plant cell of claim 2.

4. A seed comprising a transgenic plant cell of claim 2.

5. The plant transformation vector of claim 1 wherein the polynucleotide comprises the sequence of SEQ ID NO.: 1.

6. A plant cell comprising the plant transformation vector of claim 5.

7. A transgenic plant comprising a plant cell of claim 6.

8. A seed comprising a plant cell of claim 6.

9. A plant transformation vector comprising a polynucleotide effective to render a plant resistant or tolerant to infection by a tospovirus wherein the polynucleotide hybridizes under stringent conditions to a polynucleotide comprising nucleotides 3813 to 4721 of SEQ ID NO: 1, and wherein the polynucleotide is operatively linked to a plant effective transcriptional promoter.

10. A plant cell comprising the plant transformation vector of claim 9.

11. A transgenic plant comprising a plant cell of claim 10.

12. A seed comprising a plant cell of claim 10.

13. The plant transformation vector of claim 6, wherein the polynucleotide comprises polynucleotides 3813 to 4721 of SEQ ID NO.: 1.

14. A plant cell comprising the plant transformation vector of claim 13.

15. A transgenic plant comprising a plant cell of claim 14.

16. A transgenic seed comprising a plant cell of claim 14.

17. A microbiological process for making virus tolerant or resistant plants, comprising the steps of: (i) transforming regenerable plant material with a polynucleotide comprising a sequence which hybridizes under stringent conditions to a polynucleotide having the sequence of SEQ ID NO.: 1, or to a polynucleotide comprising nucleotides 3813 to 4721 of SEQ ID NO.: 1 (ii) regenerating the transformed regenerable plant material into a morphologically normal fertile plant; and (iii) selecting a plant that displays resistance or tolerance when exposed to a virus.

18. The process of claim 17, further comprising selfing the selected plant of claim 17 thereby yielding a substantially homogenous line with respect to virus tolerance or resistance trait.

19. The process of claims 18, further comprising crossing the substantially homogenous line with a second plant line.

20. The process of claim 17, wherein the polynucleotide comprises the sequence of SEQ ID NO.: 1 or nucleotides 3813 to 4721 of SEQ ID NO.: 1.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 4821 base pairs
      (B) TYPE: nucleic acid
      (C) STRANDEDNESS: double
      (D) TOPOLOGY: unknown    (iii) HYPOTHETICAL: NO    (iii) ANTI-SENSE: NO    (vi) ORIGINAL SOURCE:
      (A) ORGANISM: Tospovirus    (xi) SEQUENCE DESCRIPTION: SEQ ID NO: 1:

```
AGAGCAATCA GTGCAAACAA AAACCTTAAT CCAGACATCT TGAAATTAAT CACACAACCA      60

TTGTAATCTG GGTAGACATC TAAGATGAGA ATTCTAAAAC TACTAGAACT AGTGGTAAAA     120

GTGAGTCTTT TCACAATTGC CCTGAGTTCT GTTTTGTTGG CATTCTTGAT CTTCAGAGCC     180

ACAGATGCTA AAGTAGAAAT AATTCGTGGA GATCATCCTG AGATTTATGA TGATTCTGCT     240

GAGAATGAGG TACCCACTGC TGCATCGATT CAACGCGAAG CTATCTTAGA GACTTTAACT     300

AATCTGATGC TAGAATCTCG GACTCCTGGA ACCCGTCAGA TACGAGAAGA AAAATCAACC     360

ATCCCTATTT CTGCTGAGCC AACAACGCAA AAAACAATCT CTGTTTTGGA TCTTCCCAAC     420

AATTGCTTGA ATGCTTCTTC ATTAAAATGT GAGATAAAAG GGATATCCAC TTATAATGTT     480

TATTATCAAG TTGAAAACAA TGGTGTCATA TATTCCTGTG TTTCTGATTC AGCAGAAGGT     540

TTAGAAAAAT GTGATAATTC TTTAAATTTG CCAAAGAGAT TCTCCAAAGT CCCGGTTATT     600
```

```
CCCATTACCA AGCTAGACAA GAAAAGACAC TTTTCAGTAG GAGGAAAATT CTTCATTTCA    660

GAAAGCCTGA CACAAGATAA TTATCCTATA ACTTACAACT CATACCCCAC TAATGGAACA    720

GTATCATTAC AAACTGTAAA GTTATCCGGT GACTGCAAAA TAACTAAATC AAACTTCGCA    780

AATCCCTATA CTGTAAGCAT CACTAGCCCT GAGAAGATCA TGGGTTATTT GATAAAAAAA    840

CCTGGTGAAA ATGTGGAACA CAAGGTTATA TCTTTTTCTG GATCAGCAAG TATCACTTTT    900

ACTGAGGAAA TGTTGGATGG TGAACACAAT CTCTTGTGTG GTGACAAATC AGCCAAAATA    960

CCAAAAACAA ACAAAAGAGT CAGAGATTGC ATAATCAAAT ATTCAAAAAG TATTTATAAG   1020

CAAACAGCCT GCATCAATTT TTCTTGGATA AGGTTGATAT TGATAGCTTT GTTGATCTAT   1080

TTCCCTATCC GATGGTTAGT GAACAAGACG ACTAAACCTC TCTTTCTCTG GTATGATCTT   1140

ATGGGCTTGA TTACATACCC TGTCTTATTG CTCATAAATT GCTTATGGAA ATATTTCCCA   1200

TTAAAATGTT CTAACTGCGG CAATCTGTGC ATAGTCACAC ATGAGTGTAC TAAAGTCTGC   1260

ATTTGCAACA AAAGCAAAGC TTCAAAAGAG CATTCTTCAG AGTGTCCCAT ACTATCCAAA   1320

GAAGCAGATC ATGACTACAA CAAACATAAG TGGACTAGCA TGGAATGGTT CCATCTAATA   1380

GTGAACACTA AGCTGAGCTT GAGTTTGCTA AAATTTGTGA CCGAAATTTT GATAGGTTTA   1440

GTCATTTTGT CTCAGATGCC CATGTCTATG GCTCAAACAA CCCAATGTTT GAGTGGATGC   1500

TTTTATGTTC CAGGCTGTCC ATTTTTGGTT ACAAGCAAAT TTGAAAAATG CTCTGAAAAA   1560

GATCAATGTT ACTGCAATGT AAAAGAAGAT AAGATCATAG AGAGTATCTT TGGCACTAAT   1620

ATTGTTATAG AAGGTCCTAA TGATTGCATA GAGAACCAGA ATTGCATTGC ACGCCCATCT   1680

ATTGATAATC TTATAAAATG CAGATTAGGT TGCGAATACC TAGATTTATT CCGAAACAAA   1740

CCTTTGTACA ATGGGTTTTC GGATTATACA GGAAGCTCTT TAGGGTTAAC ATCAGTTGGT   1800

CTGTATGAGG CTAAGAGATT GAGAAATGGT ATAATAGATT CCTATAACCG TCAGGGCAAA   1860

ATTTCTGGAA TGGTTGCCGG AGACTCCTTA AACAAAAACG AAACAAGCAT ACCAGAGAAC   1920

ATTCTGCCCA GGCAATCATT AATCTTTGAT TCTGTTGTAG ACGGGAAATA TAGATATATG   1980

ATAGAACAAT CTCTTTTAGG AGGAGGAGGA ACTATATTCA TGCTAAATGA CAAGACCTCA   2040

GAAACAGCCA AAAATTTGT GATTTATATC AAAAGTGTGG GAATTCATTA TGAAGTGTCA   2100

GAAAAATATA CGACAGCTCC CATCCAAAGC ACCCACACGG ATTTTTATTC CACTTGTACA   2160

GGAAACTGCG ACACTTGCAG GAAAAATCAA GCTTTAACAG GTTCCAAGA TTTTTGTGTA   2220

ACACCAACTT CTTATTGGGG ATGTGAAGAA GCTTGGTGTT TTGCAATTAA TGAGGGTGCT   2280

ACATGCGGAT TCTGTCGAAA TATTTATGAT ATGGACAAAT CATACAGAAT TTATTCAGTG   2340

CTTAAGTCAA CTATAGTAGC AGATGTTTGT ATTTCCGGTA TTTTGGGAGG TCAATGCTCA   2400

AGGATTACTG AAGAGGTTCC TTATGAAAAT ACATTGTTTC AAGCTGATAT ACAAGCAGAT   2460

TTGCATAATG ATGGTATCAC TATAGGTGAA CTAATAGCTC ATGGACCCGA CAGTCATATT   2520

TACTCTGGAA ATATTGCAAA CTTGAATGAT CCTGTGAAAA TGTTTGGTCA TCCACAATTG   2580

ACCCATGATG GAGTGCCTAT TTTTACTAAG AAAACTCTAG AAGGAGATGA CATGTCTTGG   2640

GATTGTGCAG CAATAGGGAA AAAATCAGTC ACTATCAAAA CATGTGGATA CGACACATAC   2700

AGGTTTAGAT CTGGTTTAGA GCAAATATCA GATATTCCTG TTAGTTTCAA AGATTTTCT   2760

AGTTTTTTTC TGGCAAAATC TTTTAGTCTA GGGAAACTGA AAATGGTAGT TGATCTTCCA   2820

TCTGATCTTT TTAAAGTTGC TCCTAAGAAA CCTTCCATAA CTTCAACAAG CTTAAATTGC   2880

AATGGCTGTC TTCTATGCGG CCAAGGTTTA TCTTGCCTTT TAGAATTTTT CTCAGATTTG   2940
```

-continued

```
ACATTTTCTA CTGCAATTTC TATAGATGCT TGCTCTTTAT CTACTTATCA GCTAGCTGTT    3000

AAAAAAGGAT CTAATAAATA CAATATAACA ATGTTTTGTT CAGCCAATCC GGACAAGAAG    3060

AAAATGACAT TGTATCCAGA AGGCAATCCG GATATCTCTG TGGAAGTTTT GGTTAATAAT    3120

GTTATTGTAG AAGAACCAGA GAATATAATA GATCAAAATG ATGAGTATGC TCATGAAGAA    3180

CAACAATATA ATTCTGATTC TTCAGCATGG GGCTTCTGGG ATTATATTAA GAGTCCATTC    3240

AATTTCATTG CAAGTTACTT TGGCTCATTT TTTGATACTA TCAGAGTGGT ACTGCTTATT    3300

GCATTCATTT TTCTTGTGAC TTATTTCTGT TCTATTCTGA CATCCATTTG TAAAGGATAT    3360

GTAAAGAATG AATCTTATAA ATCTAGATCC AAGATAGAGG ATGATGATGA ACCTGAGATC    3420

AAAGCCCCTA TGTTAATGAA AGATACAATG ACAAGAAGAA GGCCACCTAT GGATTTCTCT    3480

CACCTTGTCT GAAGATGCTT GTCACAGATT AAATTTGATT CAATCTTCTA TATTAGCAGG    3540

ATTATATATA TAGAAAAATC TTTAAAATCA ATCATTAACT AATAAAAACG AAATATAAAA    3600

TAAACAAAAA ACAAACAAAA AAATAAAAAT AAACAAAAAA CAACAAAAAA AGTCTTCGGA    3660

CCAAAGTTTG CTTTTCAGCC TTATTTTGTT TTTGTTTTTT GGTTTGATTT TTTGTTTTTT    3720

TCTCTTTTTT GTTTTCGTTT TTTGTTTGGG TTTTTGGATT CAAAATGCAA AATAGACAGA    3780

AATTTAAGCT TAAATAAGTG ATATTTAAAG AACTATATTT CATCAAAGGA TAACTGAGCA    3840

ACACTGTCAG AAATTCCTTC CTCTTCCTCT TCAACTGATC TCTCAAGATT TGAGCTCAGT    3900

TCTTTAAGCT GTTTTTTTAT CTGCTTCTCA CTGTTTCCTT TAGGAATTAT CAGCTTGCAG    3960

GCTTCAATGA ATGCCTGAGA TCTAGCTCTA ATGGCCCTGT TTAGAGGTAT AACCATACAA    4020

CTTTTGTCTT TATCAGCTCT GGGTGAATCA CCAAACTCTT TTGTCCAAGA ATACATGACA    4080

CTACCAAAAG AAACCCCTTT CTTGTATTCT TGGCTACACA TCAAATGCAG CTGACAACAG    4140

TTTTCTGGGG TGTTGTTCAT CTTCGGAATA GACCAGTTCA GATAAAAAAC AAAGCAGATA    4200

GGATCAGTTA TTGTCCCCTG ACCCTTCAGG ATGACTTGCT TTCCAGATGG CATGTTGGGA    4260

TCAATTAAAG CAACCACAAG TTTTCCTGTA GGGTTTGGTA TAGTGGGGCA GACCCATATC    4320

ACAATTCTGG AAATCATCAT GTATTGTTTT CTGCTGTCCC AAGTCGGACA GATCTTGATA    4380

ACCTTATTAG CATTTTGCTT TCCGTTGCCA ACAAAAAGAT CATTTTTCCA GTTTGAGATA    4440

TGATGGTTTG TATCTACTAT CATTCTAGCA GAAAGATCAT AACCTTCTGA CTCTGTGATG    4500

GAATCAGATT CATAGGTTCC AAAGGAAGAT GTTCCCTCAA TGTTTAACAG TATCTTTCCT    4560

TTGGATGCAT CCATGGCTTT GGTTAAAGCA AGCTTTTCAT CAGAAGAAGA CCATGGTTTT    4620

GAGACTTCAA CACTGCCATT ATGTTTAGCA AGTGAAACTA AAGGACCTTC ATCCTTTCCG    4680

GCAGACTTAG AAGGCCTCTT GTTACCGAAA AGAGTCAACA TTTCGAGTTC AACAGCCTAA    4740

GGTAGAGGAG CTTGTGTAAT GTAGTTGATT GATTCTTAGC AAAATGTATA ATAGGTATAT    4800

TTCTGATGCA CTGATTGCTC T                                             4821
```

(2) INFORMATION FOR SEQ ID NO: 2:

(i) SEQUENCE CHARACTERISTICS:
        (A) LENGTH: 27 base pairs
        (B) TYPE: nucleic acid
        (C) STRANDEDNESS: both
        (D) TOPOLOGY: unknown     (iii) HYPOTHETICAL: NO     (iii) ANTI-SENSE: NO     (vi) ORIGINAL SOURCE:
        (A) ORGANISM: primer -continued

```
    (xi) SEQUENCE DESCRIPTION: SEQ ID NO: 2:

GGGAATTCTT TTCGGTAACA AGAGGCC                                          27

(2) INFORMATION FOR SEQ ID NO: 3:

(i) SEQUENCE CHARACTERISTICS:
        (A) LENGTH: 35 base pairs
        (B) TYPE: nucleic acid
        (C) STRANDEDNESS: both
        (D) TOPOLOGY: unknown (iii) HYPOTHETICAL: NO (iii) ANTI-SENSE: NO (vi) ORIGINAL SOURCE:
        (A) ORGANISM: primer (xi) SEQUENCE DESCRIPTION: SEQ ID NO: 3:

CCCTGCAGGA TCCGAAATTT AAGCTTAAAT AAGTG                                 35

(2) INFORMATION FOR SEQ ID NO: 4:

(i) SEQUENCE CHARACTERISTICS:
        (A) LENGTH: 25 base pairs
        (B) TYPE: nucleic acid
        (C) STRANDEDNESS: both
        (D) TOPOLOGY: unknown (iii) HYPOTHETICAL: NO (iii) ANTI-SENSE: NO (vi) ORIGINAL SOURCE:
        (A) ORGANISM: primer (xi) SEQUENCE DESCRIPTION: SEQ ID NO: 4:

GATCCGGCAA CGAAGGTACC ATGGG                                            25

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: both
        (D) TOPOLOGY: unknown (iii) HYPOTHETICAL: NO (iii) ANTI-SENSE: NO (vi) ORIGINAL SOURCE:
        (A) ORGANISM: primer (xi) SEQUENCE DESCRIPTION: SEQ ID NO: 5:

GCCGTTGCTT CCATGGTACC CTTAA                                            25
```